(12) United States Patent
Burbar

(10) Patent No.: US 7,873,405 B2
(45) Date of Patent: Jan. 18, 2011

(54) AUTOMATED DETECTION OF ALZHEIMER'S DISEASE BY STATISTICAL ANALYSIS WITH POSITRON EMISSION TOMOGRAPHY IMAGES

(75) Inventor: Ziad Burbar, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 672 days.

(21) Appl. No.: 10/858,637

(22) Filed: Jun. 2, 2004

(65) Prior Publication Data

US 2005/0273007 A1 Dec. 8, 2005

(51) Int. Cl.
*A61B 6/00* (2006.01)
(52) U.S. Cl. ...................................... 600/436
(58) Field of Classification Search ................. 600/436, 600/410, 411; 250/363.3, 363.4
See application file for complete search history.

(56) References Cited

U.S. PATENT DOCUMENTS

| 5,109,868 | A | 5/1992 | Smith et al. | |
|---|---|---|---|---|
| 5,873,823 | A | 2/1999 | Eidelberg et al. | |
| 6,067,542 | A | * | 5/2000 | Carino, Jr. ...................... 707/4 |
| 6,374,130 | B1 | | 4/2002 | Reiman |
| 6,381,537 | B1 | * | 4/2002 | Chenault et al. ............. 701/209 |
| 6,569,403 | B1 | | 5/2003 | Metz et al. |
| 2002/0103429 | A1 | * | 8/2002 | deCharms .................... 600/410 |
| 2005/0215889 | A1 | * | 9/2005 | Patterson .................... 600/436 |

FOREIGN PATENT DOCUMENTS

JP 10512784 T 12/1998

WO WO 02061457 A2 8/2002

OTHER PUBLICATIONS

Herholz, K. et al., "Discrimination Between Alzheimer Dementia and Controls by Automated Analysis of Multicenter FDG PET," NeuroImage. 2002; 17:302-316.

Lancaster, J.L. et al., "Automated Labeling of the Human Brain: A Preliminary Report on the Development and Evaluation of a Forward-Transform Method," Human Brain Mapping, 1997, 5:238-242.

Silverman et al., "Positron Emission Tomography in Evaluation of Dementia," JAMA, 2001, 286:2120-2127.

(Continued)

*Primary Examiner*—Tse Chen
*Assistant Examiner*—Elmer Chao
(74) *Attorney, Agent, or Firm*—Peter L. Kendall

(57) ABSTRACT

A method for detecting Alzheimer's disease using positron emission tomography. A normal population mean is obtained using PET. The normal population mean is obtained through the assimilation of a number of normal brain scans. Non-AD images and AD images are compared to observe differences in the uptake of FDG. PET scan results are expressed as relative uptake intensities and indexed by Brodmann's areas. An image is tested by comparing the distance of each mean for each Brodmann's area from the normal distribution. A Receiver Operating Characteristic curve is plotted based on the variation of deviation for the total population of both normal and probable Alzheimer's brain images. Variations in FDG uptake in a brain image as compared to the normal distribution confirms the probability of AD.

5 Claims, 8 Drawing Sheets

OTHER PUBLICATIONS

Alexander, G.E. et al., "Longitudinal PET Evaluation of Cerebral Metabolic Declines in Dementia: A Potential Outcome Measure in Alzheimer's Disease Treatment Studies," Am. J. Psychiatry, 2002, 159:738-745.

Herholz, K. et al., "Comparibility of FDG PET Studies in Probable Alzheimer's Disease," The Journal of Nuclear Medicine, 1993, 34:1460-1466.

Friston, K.J. et al., "Statistical Parametric Maps in Functional Imaging: A General Linear Approach," Human Brain Mapping, 1995, 2:189-210.

Talairach, J. et al., "Co-Planar Stereotaxic Atlas of the Human Brain: Three-Dimensional Proportional System," New York: Thierne Medical Publishers (1988).

The University of Texas, Health Science Center at San Antonio, "The MNI Brain and the Talairach Atlas," http://www.mrc-cbu.cam.ac.uk/Imaging/Common/mnispace.shtml, accessed Aug. 25, 2004.

Crivello, F., et al., "Comparison of Spatial Normalization Procedures and Their Impact on Functional Maps," Human Brain Mapping, 2002, 16:228-250.

Lancaster, J.L. et al., "Automated Talairach Atlas labels for Functional Brain Mapping," Human Brain Mapping, 2000, 10:120-131.

Sakamoto, S. et al., "Differences in Cerebral Metabolic Impairment between Early and Late Onset Types of Alzheimer's Disease," Journal of the Neurological Sciences, 2002, 200:27-32.

Silverman, D. et al., "Brain F-FDG PET in the Diagnosis of Neurodegenerative Dementias: Comparison with Perfusion SPECT and with Clinical Evaluations Lacking Nuclear Imaging," Journal of Nuclear Medicine, 2004, 45:594-607.

Pietrini, P. et al., "The neurometabolic landscape of cognitive decline: in vivo studies with positron emission tomography in Alzheimer's disease," Int'l Journal of Psychophysiology, 2000, 87-98.

Herholz, K. et al., "Criteria for the Diagnosis of Alzherimer's Disease with Positron Emission Tomography," Dementia, 1990, 1:156-164.

Thompson, P. et al., "Detecting Disease-Specific patterns of Brain Structure Using Cortical Pattern Matching and a Population-Based Probabilistic Brain Atlas," IPMI2001, LNCS 2082, 2001, 488-501.

Notification of Transmittal of the International Search Report and the Written Opinion of the International Searching Authority or the Declaration.

Minoshima S., et al., "A Diagnostic approach in Alzheimer's Disease Using Three-Dimensional Stereotactic Surface Projections of Fluorine-18-FDG PET",Journal of Nuclear Medicine, Society of Nuclear Medicine, Reston, VA, US, vol. 36, No. 7, Jul. 1, 1995 (XP002455923).

Herholz K., et al., "Discrimination between Alzeheimer Dementia and Controls by Automated Analysis of Multicenter FDG PET", Neuroimage, vol. 17, No. 1, Sep. 2002 (XP002537652).

Kippenhan J. S., et al., "Neural-Network Classifciation of Normal and Alzheimer's Disease Subjects Using High-Resolution and Low-Resolution PET Cameras", The Journal of Nuclear Medicine, vol. 35, No. 1, 1994, pp. 7-15 (XP002537653).

Ishii K. et al., "Statistical Brain Mapping of 18F-FDG PET in Alzheimer's Disease: Validation of Anatomic Standardization for Atrophied Brains" The Journal of Nuclear Medicine, vol. 42, No. 4, Apr. 2001, pp. 548-557, (XP002537654).

Herholz K., et al., "Comparability of FDG PET studies in Probable Alzheimer's Disease", The Journal of Nuclear Medicine, vol. 34,, No. 9, Sep. 1993, pp. 1460-1466, (XP 022537655).

Lancaster, J L, et al, "Automated Talairach Atlas Labels for Functional Brain Mapping", Wiley -Liss, New York, NY, vol. 10, Jan. 1, 2001, pp. 120-131, (XP008078122).

* cited by examiner

AUTOMATED DETECTION OF ALZHEIMER'S DISEASE BY STATISTICAL ANALYSIS WITH POSITRON EMISSION TOMOGRAPHY IMAGES

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

The present invention pertains to the field of Positron Emission Tomography (PET) imaging. More particularly, this invention is related to the use of PET imaging for the detection of Alzheimer's disease.

2. Description of the Related Art

Alzheimer's disease (AD) is one of several neurodegenerative diseases characterized clinically by progressive dementia. It is well known that diagnosis of AD typically relies on the demonstration of distinctive histopathologic changes in a biopsy specimen, or is determined at autopsy. Routinely practiced clinical diagnosis of AD remains largely a diagnosis of exclusion, relying on standardized tests of mental function to document dementia and a battery of various other tests to rule out alternative toxic, metabolic, or structural etiologies. A substantial body of evidence has accrued suggesting the utility of $^{18}$F-2-fluoro-2-deoxy-D-glucose (FDG) Positron Emission Tomography (PET) in the clinical diagnosis of AD. UCLA studies, for example, show that PET is 93% sensitive and 76% specific for detection of AD, as discussed by Silverman et al., "Positron Emission Tomography in Evaluation of Dementia," *JAMA*, 286:2120-2127 (2001). This reduction of FDG uptake translates to lower intensity in the image with respect to areas in the brain affected by the dementia. Classification of a pattern of reduced uptake typically relies on visual cues in the scan image and on extensive clinical experience.

Many studies identify AD by the comparison of the brains of AD patients to brains of subjects without AD. This is discussed by Alexander G E, et al., "Longitudinal PET Evaluation of Cerebral Metabolic Declines in Dementia: A Potential Outcome Measure in Alzheimer's Disease Treatment Studies," *Am. J. Psychiatry*, 159:738-745 (2002). As taught by Silverman, et al., scans of a brain affected by AD reflect a heterogeneously reduced uptake of FDG in certain areas, which indicates decreased metabolic activity. Characterization of this pattern of reduced uptake is central to the assessment of PET as a diagnostic method for AD, and is essential to its application in clinical practice.

Herholz, K et al., "Discrimination Between Alzheimer Dementia and Controls by Automated Analysis of Multicenter FDG PET," *NeuroImage*, 17:302-316 (2002), demonstrated a voxel-based method that shows the reduction of the cerebral metabolic rate of glucose (CMRGlc) in Alzheimer's patients for a certain age group. In a further study, Herholz, K. et al., "Comparibility of FDG PET Studies in Probable Alzheimer's Disease," *The Journal of Nuclear Medicine*, 34:1460-1466 (1993), compared FDG uptake in different patients with probable AD from three different centers.

BRIEF SUMMARY OF THE INVENTION

The present invention is a method for detecting Alzheimer's disease (AD) using positron emission tomography (PET). The method is useful for assessment of various automated diagnostic techniques in an objective fashion, and generates data which is applicable as input to pattern recognition algorithms. In the method of the present invention, a normal population mean, or baseline brain scan, is obtained using PET technology for comparing a brain scan of a patient in order to determine whether the patient has AD or is physiologically disposed to develop AD. $^{18}$F-2-fluoro-2-deoxy-D-glucose (FDG) or other suitable PET biomarkers are used to obtain PET images for use in diagnosing AD. The baseline scan is obtained through the assimilation of a number of brain scans taken of subjects who have no known symptoms of AD, nor any known physiological predisposition of AD. The present invention serves several purposes. In addition to the present invention being useful in determining whether a patient is predisposed to AD, it also serves to determine the severity of the disease in the brain image. Further, the present invention assists in allocating the location of the disease in the brain image under test.

In the method of the present invention, test patients are scanned to verify the efficacy of the method. Each subject is injected with FDG and scanned with a PET scanner such as the ECAT EXACT HR scanner (CPS Innovations, Knoxville, Tenn.). Each subject is positioned to rest on his/her back in conditions of low light and ambient noise.

A number of confirmed non-AD brain scans are taken as described. The non-AD brain images are converted to the Montreal Neurological Institute (MNI) standard using Statistical Parametric Mapping (SPM) to conform data to a known anatomical space. The MNI images are then converted to Talairach space images using non-linear transformations to conform the images to the Talairach coordinates database.

Each image is then written into memory. Using a Talairach Daemon brain database, each Brodmann's area is determined by reconstructing an SQL statement that accesses the Talairach database. The return values are a series of X, Y, and Z dimensions for the specific Brodmann's area. The mean value of each Brodmann's area is determined separately for each right and left brain image. For each image, the data is plotted on an XY linear plot showing Brodmann's area vs. mean FDG uptake. The variance for each Brodmann's area is then calculated for each brain image.

The image data is normalized to a region in the brain that is not affected by the disease to conform it to a common base. For each image, each of the mean values for each Brodmann's area is then normalized to Brodmann's area 4, the primary somatomotor area for the left and right brain. For the total normal population, the mean value is calculated from each normalized Brodmann's area to form a population mean value for each Brodmann's area.

The variance for each Brodmann's area is then calculated for each brain image and the result is a normalized vector of Probability Density Function (PDF) for each Brodmann's area, which is the standard distribution of FDG uptake by a normal brain for each Brodmann's area.

A Gaussian distribution is assumed and a standard normal distribution table is used to verify the confidence limit by varying the standard deviation from the mean of the distribution. By setting each Brodmann's area to a Gaussian distribution with a mean and a variance, the deviation of a point under test is then calculated from the mean of the distribution.

Because a normal FDG uptake standard distribution is created, an image is tested by comparing the distance of each mean for each Brodmann's area from the normal distribution. The standard normal brain distribution and variance are read from software. The image is then examined to determine the mean value of each Brodmann's area under test. Each Brodmann's area is then normalized to Brodmann's area 4.

The method of the present invention reads and tests for the left side, the right side, and both sides of the brain.

For test purposes, brain images of confirmed AD patients are collected as described previously. Each image is converted to Talairach space and tested for AD. A test of elimination is done to determine the areas that register the largest deviation from the normal population mean.

Brain images of subjects having no known symptoms of AD, or any known physiological predisposition of AD are then collected in similar fashion. Each image is processed and compared to the normal population mean in similar fashion to the AD brain images. The images are then converted to Talairach space and tested for Alzheimer's. With a Gaussian distribution, a standard normal distribution table is used to verify the confidence limit by varying the standard deviation from the mean of the distribution.

An image is tested by comparing the distance of each mean for each Brodmann's area from the normal FDG uptake standard distribution. This test is performed where the disease might exist in the brain. Therefore, the motor, visual, lingual, and hearing portions of the brain are excluded from the test.

The expected value of each Brodmann's area for a normal brain should fall within the mean of the normal FDG uptake distribution standard. A variation from the mean is expected, since no two human brains function the same. However, the variation is higher for an Alzheimer's brain image. Therefore, by varying the deviation from the mean for a normal brain image under test, the distance from the mean increases as the deviation increases.

A Receiver Operating Characteristic (ROC) curve is plotted based on the variation of deviation for the total population of both normal and probable Alzheimer's brain images. At each deviation value, points that fall outside of the deviation distance are averaged. The points that fall outside the deviation in AD scans are considered to be true positives, and those that fall outside the deviation in normal brain scans are false positives.

The method suggests whether an image under test is a normal brain image or one with probable Alzheimer's. For those images where the results point toward Alzheimer's, the Brodmann's area in which the Alzheimer's is detected is examined more closely for further analysis.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1A:
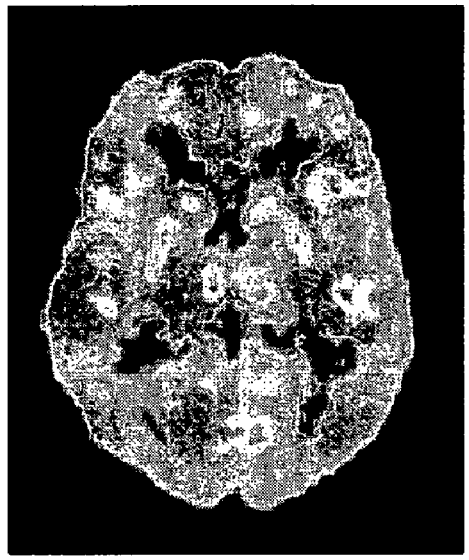
FIGS. 1A and 1B are PET images of a normal brain before and after conversion to Talairach space, respectively.

A method for detecting Alzheimer's disease (AD) using positron emission tomography (PET) is disclosed. The method of the present invention is a reproducible method for characterizing scan results for use in clinical practice. The method is useful for assessment of various automated diagnostic techniques in an objective fashion, and generates data which is applicable as input to pattern recognition algorithms. The method of the present invention provides input to a threshold-based pattern recognizer to distinguish scans of a normal population from those of patients with AD. The method of the present invention is an automated method which characterizes $^{18}$F-2-fluoro-2-deoxy-D-glucose (FDG) PET scan results to identify AD. It will be understood by those skilled in the art that other suitable PET biomarkers may be used as well. In addition to the present invention being useful in determining whether a patient is predisposed to AD, it also serves to determine the severity of the disease in the brain image. Further, the present invention assists in allocating the location of the disease in the brain image under test.

In the method of the present invention, a normal population mean, or baseline brain scan, is obtained using PET technology for comparing a brain scan of a patient in order to determine whether the patient has AD or is physiologically disposed to develop AD. The baseline scan is obtained through the assimilation of a number of brain scans taken of subjects who have no known symptoms of AD, nor any known physiological predisposition of AD. As will be discussed below, for confirmation of the efficacy of the present method, an identical process is followed for a number of subjects who have been diagnosed with AD with a comparison made to the baseline to confirm AD. As the method of the present invention is disclosed below, particulars for a test of the present method are also disclosed. It will be understood that the particulars set forth for such test are not intended to limit the present invention as such, but may be varied as required for a particular implementation of the present method.

The method of the present invention has been used in test patients to verify the efficacy of the method. For all scans in the test, each subject was injected with 10 milli-Ci of FDG and scanned with an ECAT EXACT HR scanner (CPS Innovations, Knoxville, Tenn.). In testing of the present invention, a scan length of one hour was used. However, it will be understood by those skilled in the art that the scan length may vary depending upon the particular conditions of the scan and the required accuracy of the collected data. Each subject is positioned to rest on his/her back in conditions of low light and ambient noise. In the tests described herein, a quantified image was reconstructed from t=20 minutes to t=60 minutes.

In the above-described test, differences were found in the comparison of the 16 normal and 12 AD brain images used to observe FDG uptake. A standard deviation (STD) of 0.06 was found with the six selected regions in the normal brain, whereas a higher STD of 0.23 was found in those areas for AD patients. The higher STD in the AD patients confirms AD brain images from AD patients are distinguishable over normal brain images as a result of varied FDG uptake.

PET scan results were expressed as relative uptake intensities and indexed by Brodmann's areas. The use of Brodmann's areas as anatomic and functional landmarks is well-established in medical history and clinical practice.

A number of confirmed non-AD brain scans are taken as described. In the test, forty-four confirmed non-AD FDG brain images were taken from a population of both male and female subjects having a mean age of 54±13 years. The non-AD brain images are converted to the Montreal Neurological Institute (MNI) standard using Statistical Parametric Mapping (SPM) to conform data to a known anatomical space. (see Friston K J et al., Statistical Parametric Maps in Functional Imaging: A General Linear Approach, *Human Brain Mapping*, 2:189-210 (1995).) In the test, SPM used compiled software for Windows® platforms. The MNI standard converted the size of the image to 79×95×68 pixels, with each pixel measuring 2 mm×2 mm×2 mm. The MNI images are then converted to Talairach space images using non-linear transformations. (see Talairach J. et al., *Co-Planar Stereotaxic Atlas of the Human Brain: Three-Dimensional Proportional System*, New York: Thieme Medical Publishers (1988), and The Research Imaging Center, The University of Texas, Health Science Center at San Antonio, "The MNI brain and the Talairach Atlas," http://www.mrc-cbu.carn.ac.uk/llrnaging/mnispace.html, accessed December 2002). Transforming the MNI images into Talairach space images conforms the images to the Talairach coordinates database.

Figure 1B:
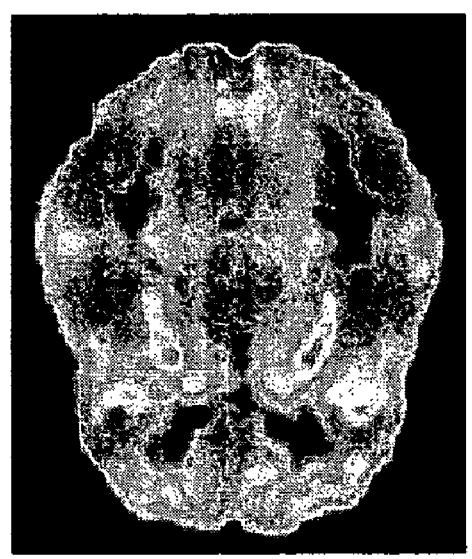
Figure 1C:
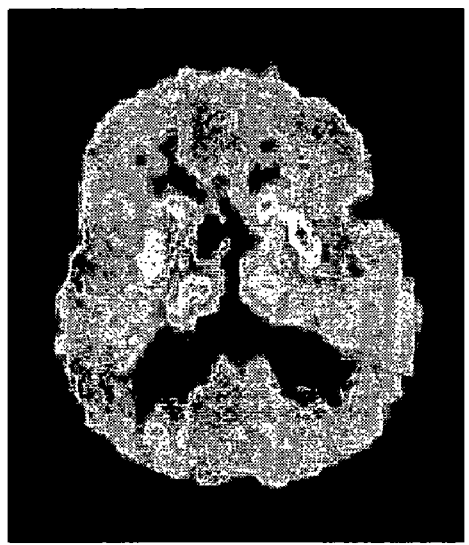
FIGS. 1C and 1D are PET images of a probable AD brain before and after conversion to Talairach space, respectively.
Figure 1D:
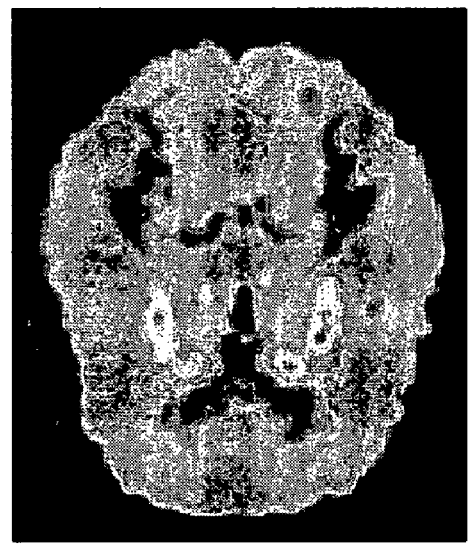

FIGS. 1A-1D are illustrative of brain images before and after conversion to Talairach space. FIGS. 1A and 1B are of a normal brain before and after conversion, respectively. FIGS. 1C and 1D are of a probable AD brain before and after conversion, respectively.

SPM was selected in the described test due to its availability and its well-documented validity. However, it will be understood that other methods are useful. These methods include, but are not limited to Simple Afine (AFF), Fifth Order Polynomial Warp (WRP), and Full Multi Grid (FMG). See, for example, Crivello F, et al., Comparison of Spatial Normalization Procedures and Their Impact on Functional Maps, *Human Brain Mapping*, 16:228-250 (2002).

Each image is then written into memory. Using a Talairach Daemon brain database, as described by Lancaster J. L. et al., Automated Talairach Atlas Labels For Functional Brain Mapping, *Human Brain Mapping*, 10: 120-131 (2000), each Brodmann's area is determined by reconstructing a Structured Query Language (SQL) statement that accesses the Talairach database. SQL is used to allow complex inquiries of a database. The return values are a series of X, Y, and Z dimensions for the specific Brodmann's area. The mean value of each Brodmann's area (1 through 47, excluding 12, 14, 15, 16, and 26) is calculated by:

$$\mu(ba) = \frac{1}{p}\sum_{i=1}^{P} vx_i,$$

where $\upsilon$ is the number of image voxels representing a Brodmann's area and $\upsilon x_i$ represents FDG uptake for each voxel in the selected Brodmann's area.

The resulting value μ(ba) represents FDG uptake for each Brodmann's area from each normal patient from both their left and right brain. The consumption of the cell and the dosage/body concentrations tend to differ for each patient. The image data is normalized to conform it to a common base. Images are normalized to a region in the brain that is not affected by the disease. For each image, each of the mean values for each Brodmann's area is then normalized to Brodmann's area 4, the primary somatomotor area for the left and right brain, using:

$$n\mu(ba) = N(ba) = \frac{\mu(ba)}{\mu(4)},$$

where nμ(ba) represents the normalized mean value of each Brodmann's area to Brodmann's area 4, and N(ba) represents the normalized Brodmann's area.

For the total normal population, the mean value is calculated from each normalized Brodmann's area to form a population mean value for each Brodmann's area using:

$$M(ba) = \overline{N(ba)} = \frac{1}{X}\sum_{i=1}^{X} N(ba)_i,$$

where X is the total number of the population in the study. In the present example, X=44. M(ba) is the population normalized mean value of each Brodmann's area.

The variance for each Brodmann's area is then calculated for each brain image using:

$$\sigma^2(N(ba)) = \frac{\sum_{i=1}^{X}(N(ba)_i - M(ba)_i)^2}{(X-1)}.$$

The result is a normalized vector of Probability Density Function (PDF) for each Brodmann's area, which is the standard distribution of FDG uptake by a normal brain for each Brodmann's area.

The relative functional preservation of the somatomotor cortex is a reliable indicator of Alzheimer's disease, as supported by other investigations, and was the reason that the area was chosen as the value against which to normalize. Sakamoto S, et al., Differences in Cerebral Metabolic Impairment between Early and Late Onset Types of Alzheimer's Disease, *Journal of the Neurological Sciences*, 200:27-32 (2002). Functional preservation is noted where no degradation in uptake of FDG is revealed. However, it will be understood that other areas may be normalized with respect to another area or any function dependent on a combination of areas.

The normal brain image data is tested to determine whether a Gaussian distribution may be used. A moment analysis is used on each of the Brodmann's areas to obtain the mean and variance of the distribution. Each distribution is then fitted to a Gaussian distribution. Each Brodmann's area in the Gaussian distribution is then binned, with the number of bins being varied to match a fit. The reduced Chi square is then calculated for each bin variation. A standard normal distribution table is used to verify the confidence limit by varying the standard deviation from the mean of the distribution. kσ represents the standard deviation distance from the mean. By setting each Brodmann's area to a Gaussian distribution with a mean and a variance, the kσ of a point under test is then calculated from the mean of the distribution.

Because a normal FDG uptake standard distribution is created, an image is tested by comparing the distance of each mean for each Brodmann's area from the normal distribution. The standard normal brain distribution and variance are read from software. The image is then examined to determine the mean value of each Brodmann's area under test.

The method of the present invention reads and tests for the left side, the right side, and both sides of the brain.

For test purposes, brain images of 118 confirmed AD patients were collected as described previously. The patients were diagnosed with Alzheimer's by NINCDS-ADRDA criteria. The Alzheimer's patients were both male and female with a mean age of 65±9 years. Each image was converted to Talairach space and tested for AD. The motor, visual, lingual, and hearing portions of the brain were excluded from the test, as such areas are not affected by AD. The Brodmann's areas examined in the search for AD included areas 7, 9, 10, 11, 13, 20, 21, 22, 23, 24, 25, 28, 30, 31, 34, 35, 36, 39, and 40. A test of elimination was done to determine the areas that register the largest kσ from the normal population mean.

Next, the brain images of 46 subjects having no known symptoms of AD, nor any known physiological predisposition of AD were taken as described above. Each image was processed and compared to the normal population mean in similar fashion to the AD brain images. These 46 normal brain images were gathered from males and females with a mean age of 52±11 years. The images were converted to Talairach space and tested for Alzheimer's.

With a Gaussian distribution, a standard normal distribution table is used to verify the confidence limit by varying the standard deviation from the mean of the distribution:

$$CL(ba_t)\% = \int_{M(ba)-k\sigma(ba)}^{M(ba)+k\sigma(ba)} p(M(ba_t)) = F(M(ba) + k\sigma(ba)) - F(M(ba) - k\sigma(ba)),$$

where $p(M(ba_t))$ is the probability of the Brodmann's area mean under test being under the Gaussian distribution curve giving the limits of the mean±kσ(ba). This produces a confidence limit equation represented by $CL(ba_t)\%$.

Figure 2A:
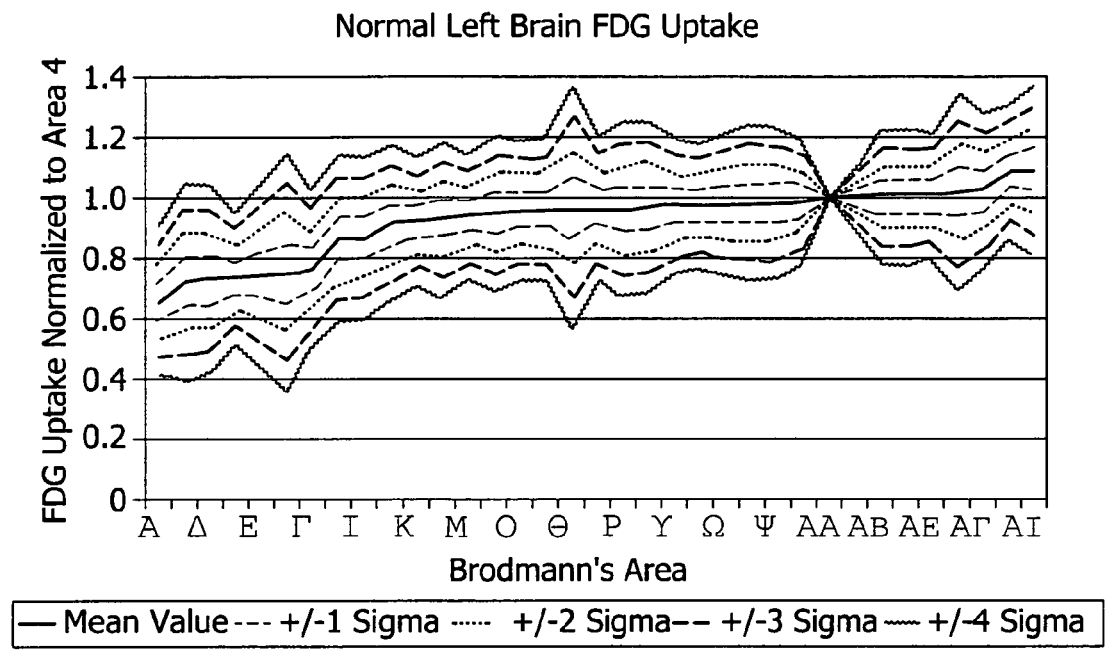
FIGS. 2A and 2B are graphic illustrations of the variation of FDG uptake in the left and right sides of the brain, respectively.
Figure 2B:
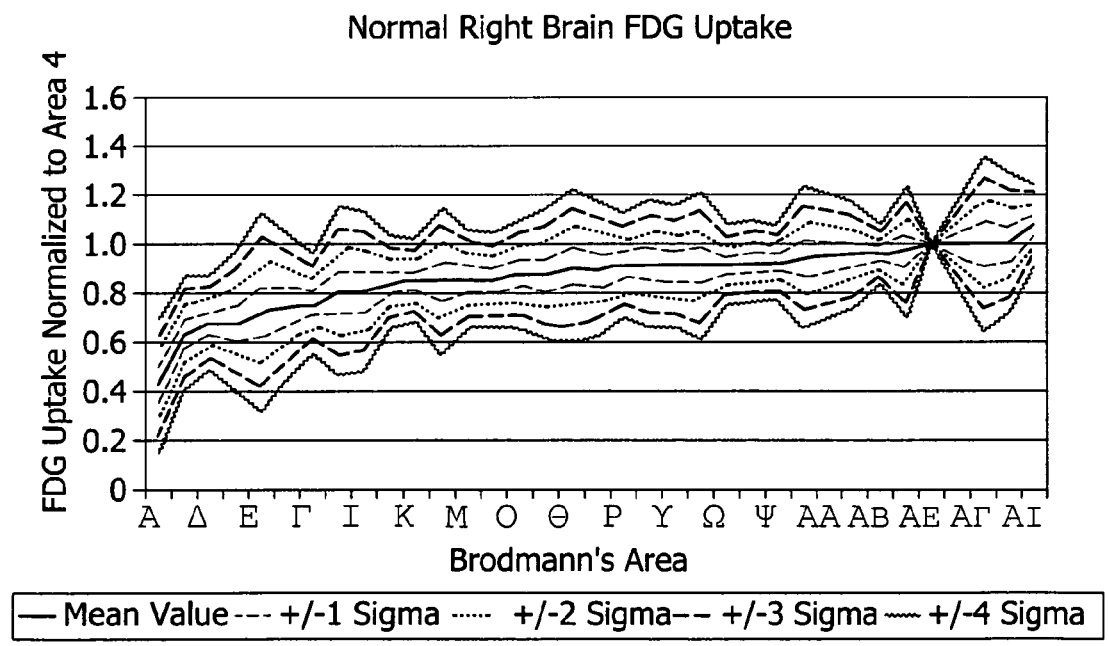
Figure 3:
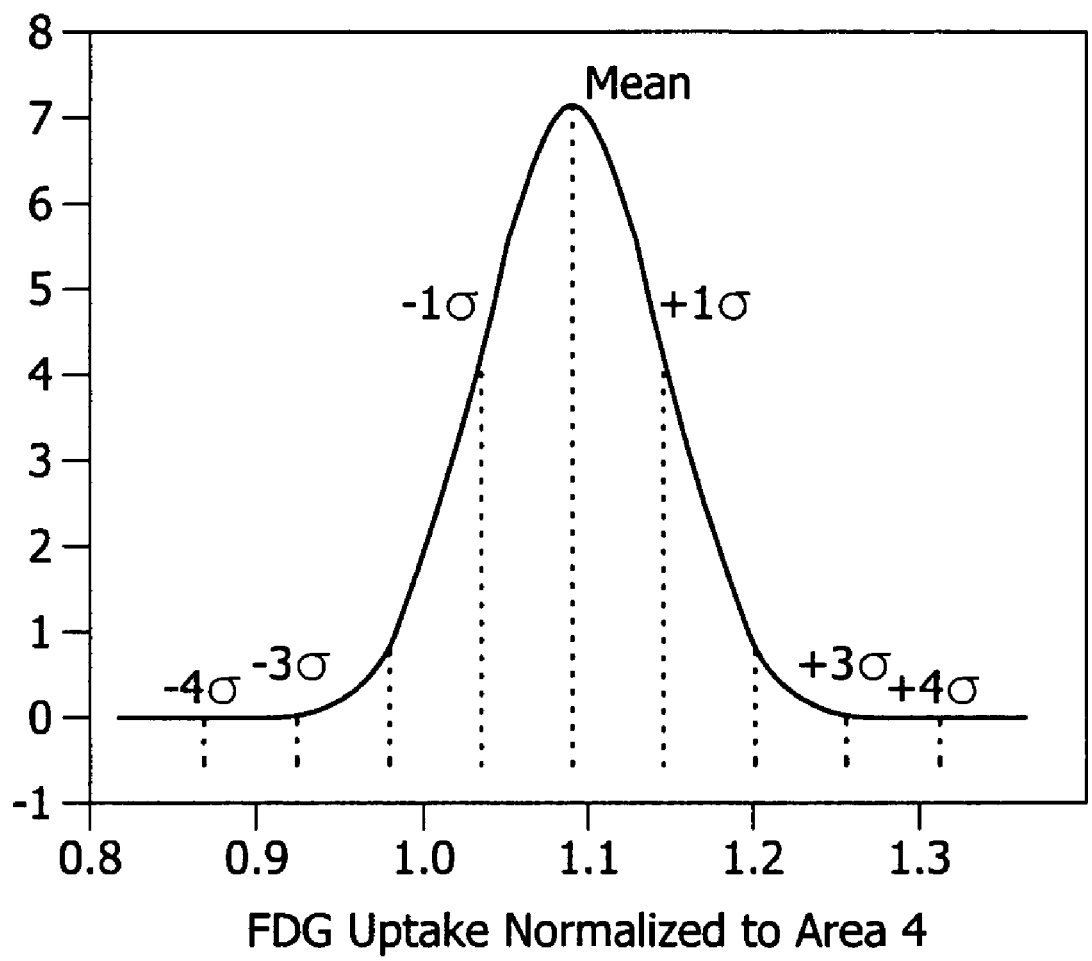
FIG. 3 is a graphical illustration of Brodmann's area 7 as a Gaussian distribution.

In the next step of developing a baseline, or normal population mean, plotting each point of the mean value of the Brodmann's areas of the 44 normal brain images showed the confidence limits when kσ varied from the mean value. FIGS. 2A and 2B illustrate the variation for the left and right brain. FIG. 2A illustrates FDG uptake in the left brain and FIG. 2B illustrates FDG uptake in the right brain. Each of the means was plotted after permutation. A limit of ±1, 2, 3 and 4 sigma was plotted to show the confidence limit of each Brodmann's area distribution. FIG. 3 illustrates Brodmann's area 7 as a Gaussian distribution, showing the ±1σ, ±2σ, ±3σ and ±4σ from the mean value of the distribution.

An image is tested by comparing the distance of each mean for each Brodmann's area from the normal FDG uptake standard distribution. This test must be performed where the disease might exist in the brain. Therefore, the motor, visual, lingual, and hearing portions of the brain are excluded from the test, since they are areas that might not be affected by AD. The Brodmann's areas examined in the search included areas 7, 9, 10, 11, 13, 20, 21, 22, 23, 24, 25, 30, 31, 34, 35, 36, 39, and 40.

The expected value of each Brodmann's area for a normal brain should fall within the mean of the normal FDG uptake distribution standard. A kσ variation from the mean is expected, since no two human brains function the same. However, the kσ variation is expected to be much higher for an Alzheimer's brain image. Therefore, by varying kσ from the mean for a normal brain image under test $M(ba_t)$, the distance from the mean should increase as kσ increases. While varying kσ for a probable Alzheimer's brain image under test $M(ba_t)$, the distance between the point under test $M(ba_t)$ and the standard FDG uptake σ(ba) for that area starts at a large value, then decreases as kσ increases. Once the point falls under the area of the distribution, the distance between the point under test and the mean starts to increase, leaving a minimum (or zero value), which indicates the limit.

Figure 4A:
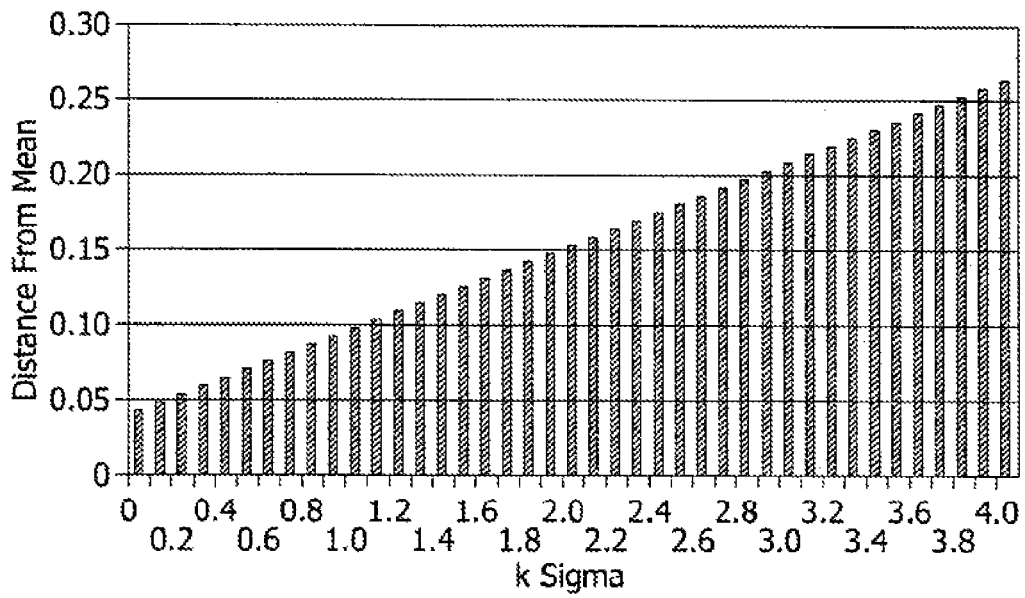
FIGS. 4A and 4B are graphic Illustrations of the distance from the mean of Brodmann's area 7 as $k\sigma$ increases in a normal brain and in an AD brain, respectively.
Figure 4B:
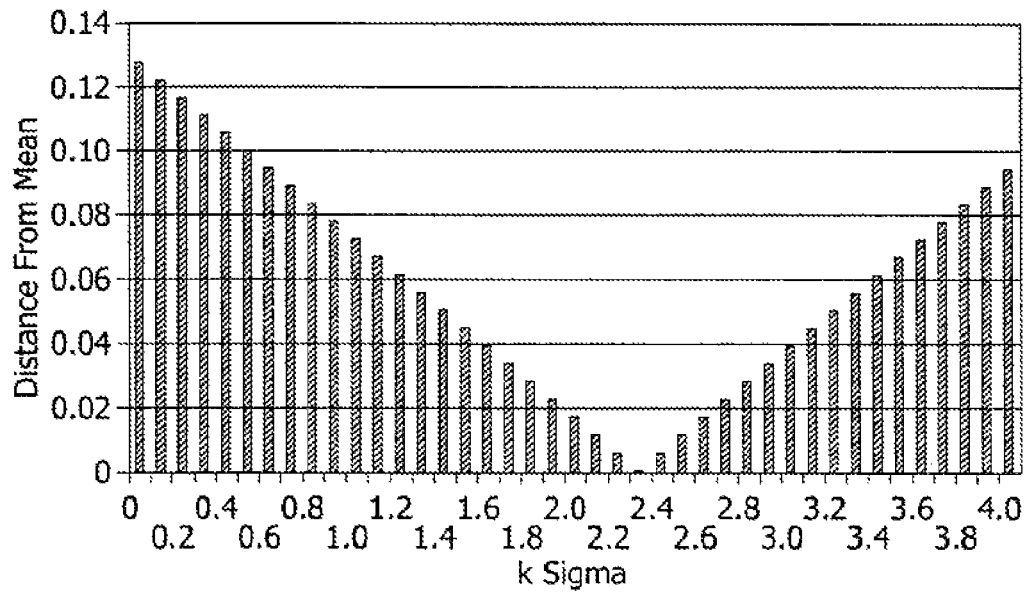

Illustrated in FIGS. 4A and 4B is a graphical comparison of Brodmann's Area 7 in normal and AD brain images. FIG. 4A illustrates the distance from the mean of Brodmann's area 7 as kσ increases in a normal brain. As kσ increases in a normal brain, the distance from the mean increases, leaving a minimum value at k=0.2. The number in the normal FDG uptake distribution standard represents the expected value for the Brodmann's area for a normal brain image. FIG. 4B illustrates Brodmann's area 7 of a probable AD brain image. The expected value is far from the mean value, and as kσ increases, the distance decreases to near zero, then increases again. The zero point in this example is at k=2.4, which results in a confidence limit of 98.36%.

Figure 5A:
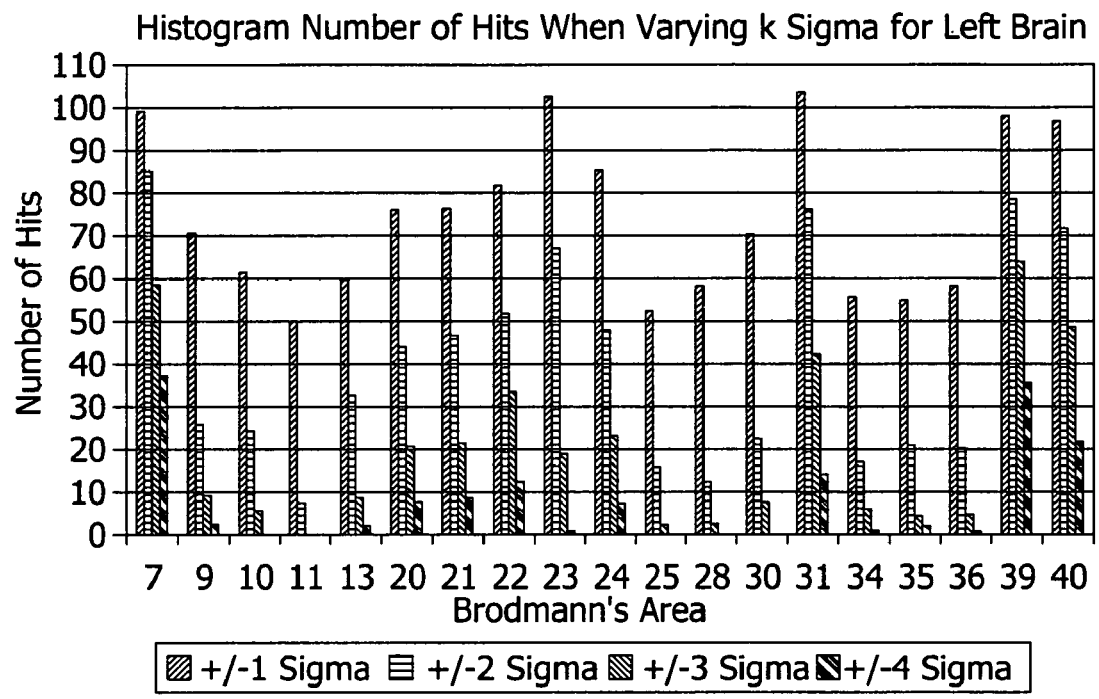
FIGS. 5A and 5B are histograms of the number of AD patients that showed deviations from the mean for certain Brodmann's areas in the left brain and the right brain, respectively.
Figure 5B:
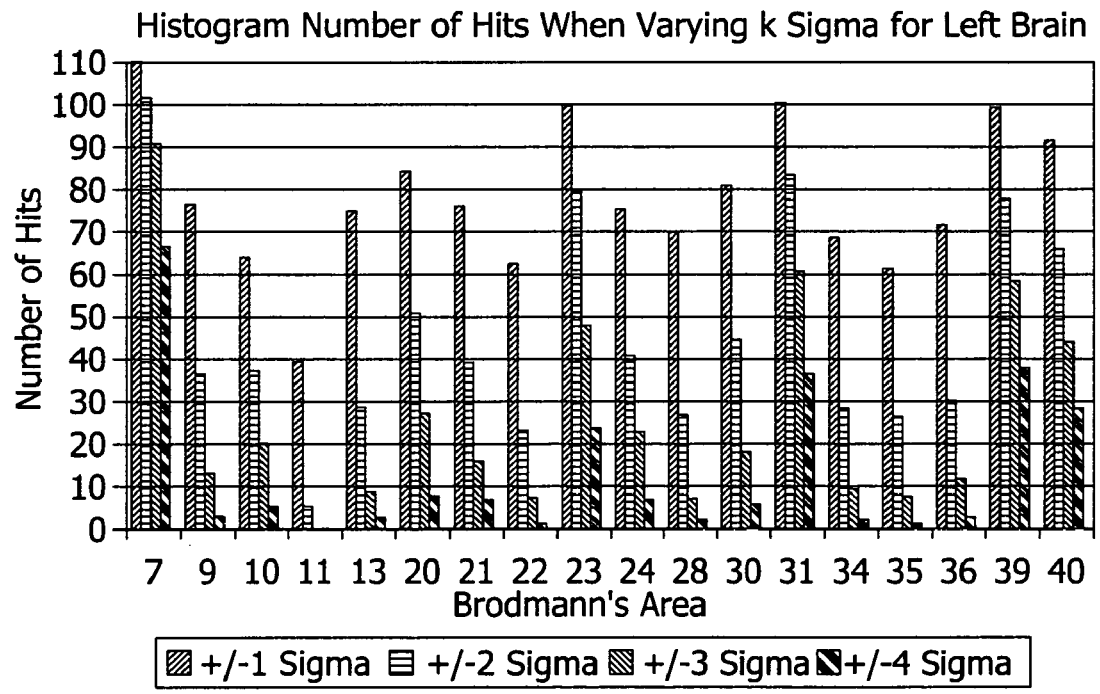

By running all confirmed AD images and compiling a database of the Brodmann's areas that register the disease at k=±1σ, ±2σ, ±3σ and ±4σ, the data is histogrammed the data to see in which common area the disease registers. FIGS. 5A and 5B illustrate diagrammatically a histogram of the number of AD patients that showed deviations from the mean for certain Brodmann's areas. FIG. 5A is a histogram of the left brain and FIG. 5B is a histogram of the right brain. Areas 7, 31, 39, and 40 showed the greatest deviations for ±3σ and ±4σ. ±3σ and ±4σ are the most significant because these reflect the most severe cases of AD. These four Brodmann's areas are located in the inward and outward portions of the back end of the parietal lobe.

Figure 6A:
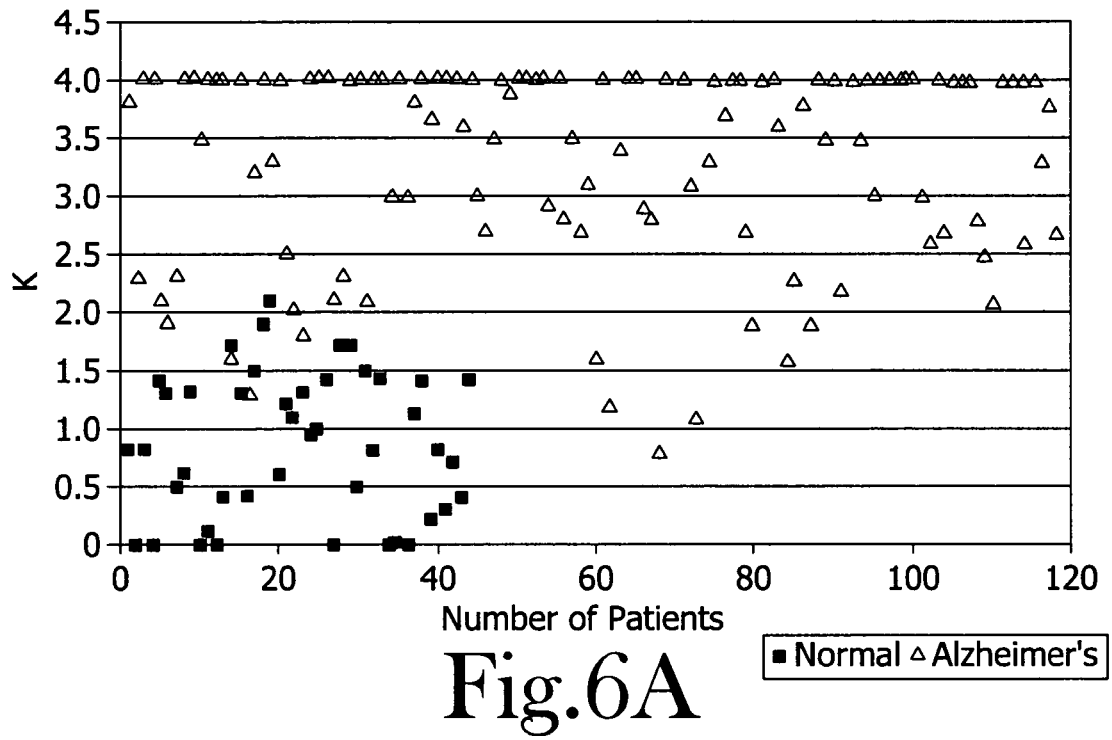
FIGS. 6A and 6B illustrate plots of the results of the farthest $k\sigma$ for each selected Brodmann's area for both the normal and the AD subjects for the left brain and the right brain, respectively.
Figure 6B:
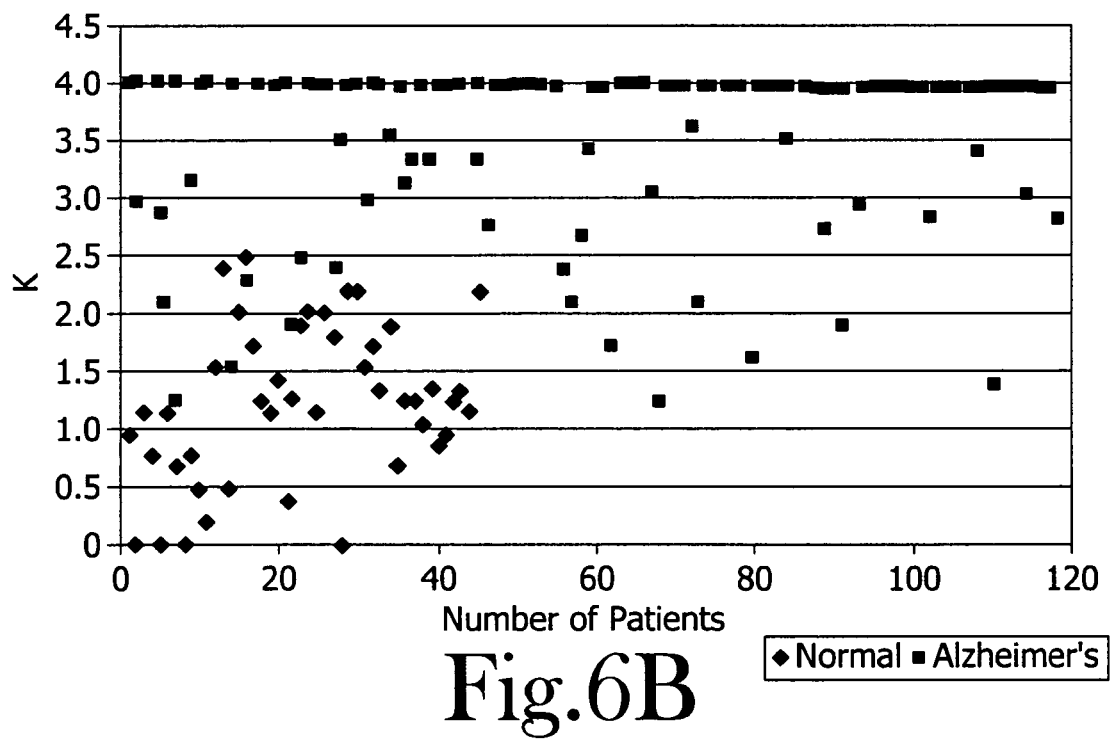

A plot of the results of the farthest kσ for each selected Brodmann's area for both the normal and the AD subjects is illustrated in FIG. 6A for the left brain and FIG. 6B for the right brain. The results of the farthest k sigma for both the normal and the Alzheimer's populations for selected Brodmann's areas can be seen. The data consist of the maximum point deviated from the standard FDG uptake and the Brodmann's area associated with it. This indicates data relative to normal brains and Alzheimer's-effected brains that are discriminated with a simple linear discriminant function as illustrated in FIGS. 5A and 5B. As shown, most of the normal population fell at k≦2. On the other hand, most of the Alzheimer's population fell at k≧2. A large number of the Alzheimer's population was saturated at k=4, which is the largest value used for k.

Finally, a Receiver Operating Characteristic (ROC) curve is plotted based on the variation of kσ for the total population of both normal and probable Alzheimer's brain images to evaluate the method. At each k value, a sum of points that fall outside of the kσ distance are added and divided by the total number of studies. The points that fell outside the kσ distance in the 118 Alzheimer's scans were considered to be true positives. The points that fell outside the kσ distance of the 46 normal brains were considered to be false positives.

Figure 7:
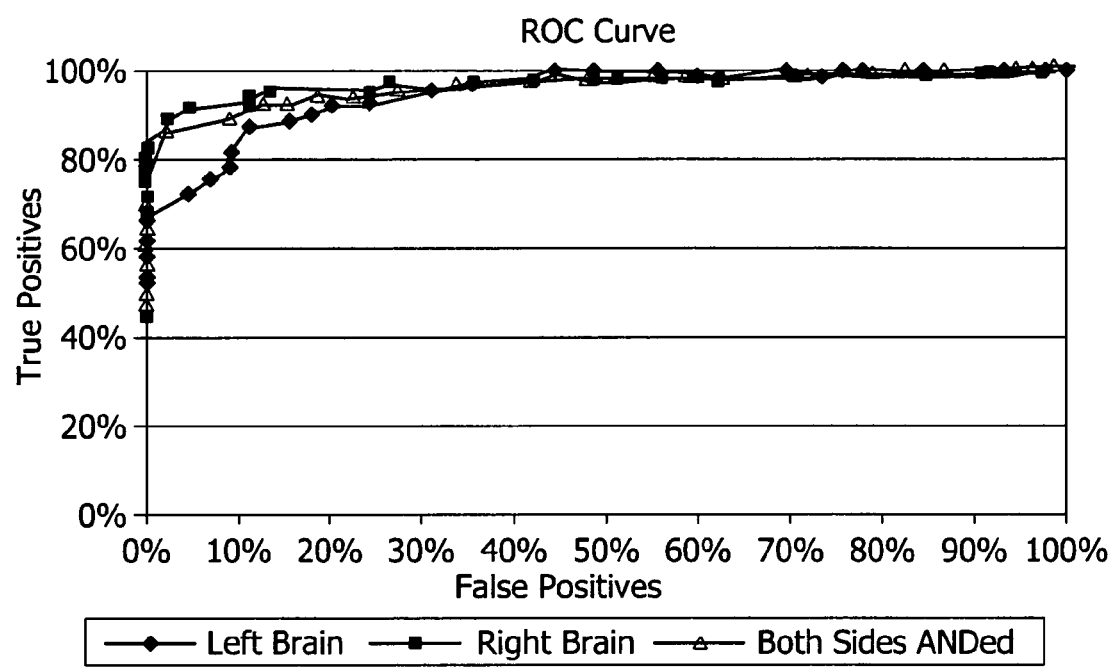
FIG. 7 is a graphical illustration of a Receiver Operating Characteristic (ROC) Curve showing true and false positives to determine whether an image under test is a normal brain image or a probable AD brain image.

FIG. 7 illustrates the ROC curve showing true and false positives. Results for both the left and right sides of the brain are shown, as well as the results, denoted "Both Sides ANDed", where both sides of the brain fell outside an acceptable range. The curve was generated by varying kσ by 0.1 from k=0 to k=4 and utilizing Brodmann's areas that fall outside of the kσ distance. For an automated method, the threshold line k is set to operate on the left side of the ROC graph. Testing has shown that k=2.2 to k=2.4 yields reasonably high true positives (TP) and low false positives (FP). Specifically, in the tests, for k=2.2, TP=90.7%, and FP=8.9%. For k=2.4, TP=87.3% and FP=2.2%.

The results suggest whether an image under test is a normal brain image or one with probable Alzheimer's. For those images where the results point toward Alzheimer's, the Brodmann's area in which the Alzheimer's is detected is examined more closely for further analysis.

The results of the test as described confirms the efficacy of the method of the present invention, which includes acquiring a standard of normalized uptake values indexed by Brodmann's area and distinguishing uptake patterns characteristic of AD from patterns characteristic of healthy patients. By normalizing to one Brodmann's area, such as area 4 which is not affected by AD, the irregularity of the image intensity is instantiated for a probable AD image. In the test as described, Brodmann's areas that are affected by AD varied widely in FDG uptake from uptake of normal brains. The same principle applied to a normal image shows Brodmann's areas fall within the standard FDG uptake due to the uniformity in the image intensity.

Figure 8A:
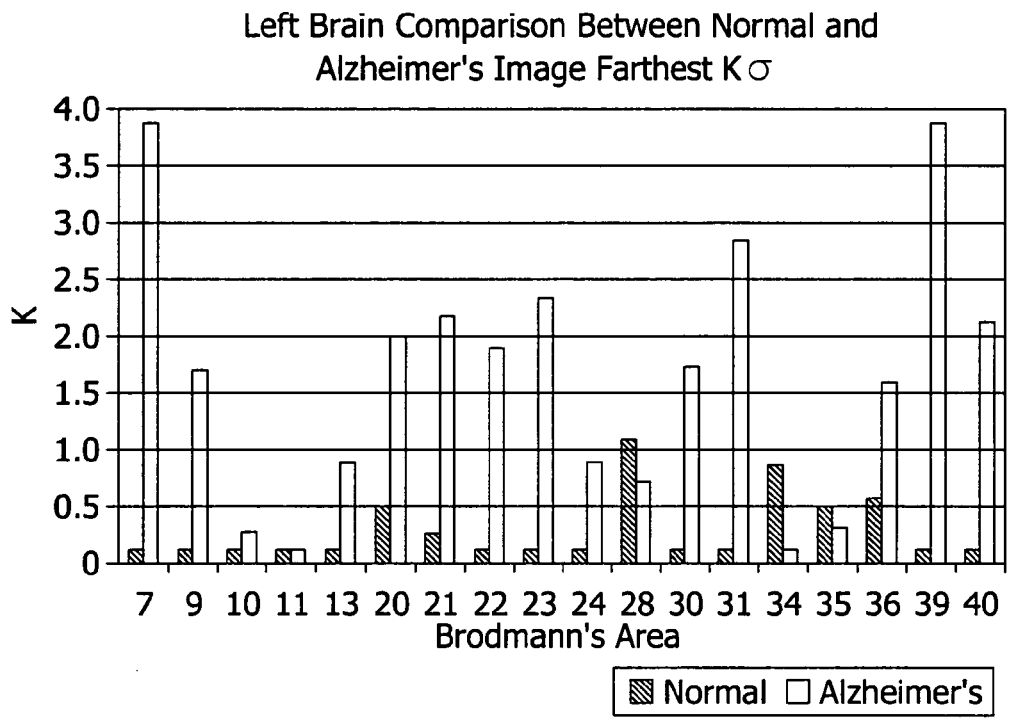
FIGS. 8A and 8B illustrate the k value registered for the left and right brain, respectively, for both normal and AD brain images.
Figure 8B:
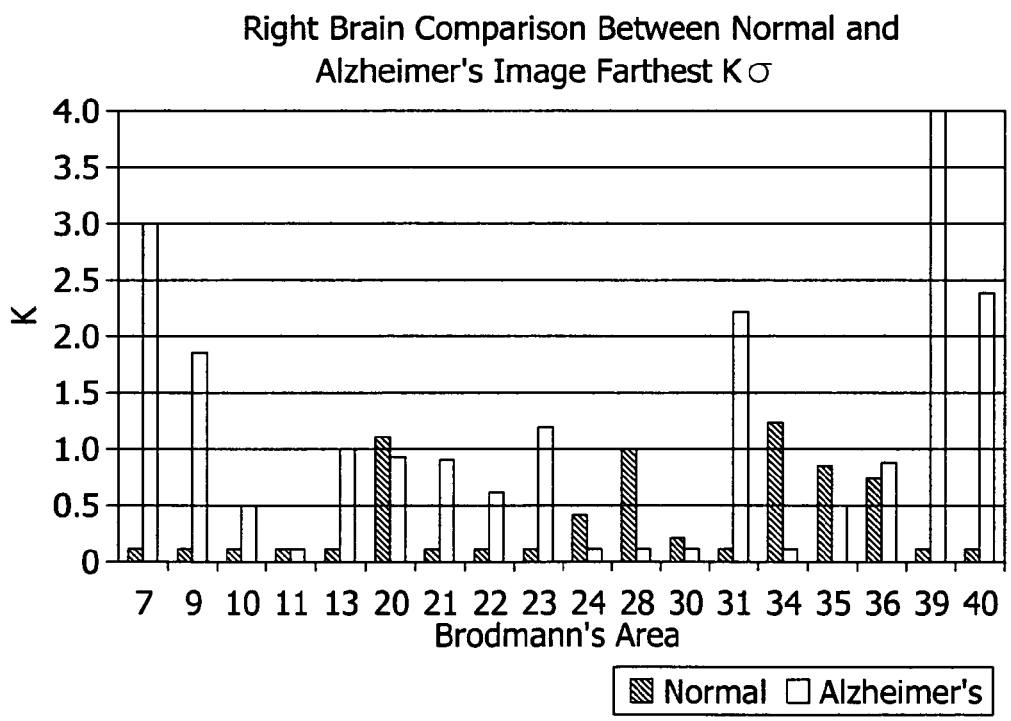

FIGS. 8A and 8B illustrate the k value registered for the left and right brain, respectively, for both normal and AD brain images shown earlier. The k value for the normal brain is mostly zero, as few Brodmann's area registered 1.1 or less. This indicates that the images of normal brains for each Brodmann's area closely follow the standard FDG uptake, whereas the images of AD brains widely differ from the standard FDG uptake by as high as k=4.0.

While validation of the present method was accomplished using a population of individuals diagnosed with AD on the basis of clinical evidence alone, it will be understood that histopathologic data from a population of individuals diagnosed with AD is anticipated as useful for such validation as well.

The method of the present invention is simple to perform and is easily reproducible. Further, the method is readily adaptable to distinguishing pathologies other than AD, such as, but not limited to, Parkinson's disease. Still further, the method of the present invention provides quantitative information that can be incorporated into computation and assessment formulas required by most basic research.

From the foregoing description, it will be recognized by those skilled in the art that a method for detecting Alzheimer's disease (AD) using positron emission tomography (PET) has been provided. The method of the present invention is provided for characterizing scan results for use in clinical practice. The method is useful for assessment of various automated diagnostic techniques in an objective fashion, and generates data which is applicable as input to pattern recognition algorithms.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, I claim:

1. A method for detecting Alzheimer's Disease (AD) using positron emission tomography (PET), comprising the steps of:
   determining preselected regions of a patient's brain for analysis, prior to any imaging of said patient's brain to obtain image data for said analysis;
   obtaining PET image data of said patient's brain using a PET imaging apparatus;
   comparing, using a processor, PET image mean intensity data of said preselected regions of said patient's brain with a standard distribution of PET image mean intensity data of corresponding regions from a database of non-AD population to determine the distance of each mean from the mean of said standard distribution;
   determining, using a processor, the variation of said distance over said preselected regions;
   determining, using a processor, the probability of AD in said patient as a function of said variation; and
   displaying on a display device the probability of AD as a result of said determining step.

2. The method of claim 1, wherein said preselected regions are preselected Brodmann's areas.

3. The method of claim 2, wherein said preselected Brodmann's areas are determined separately for a left side and a right side of said patient's brain.

4. The method of claim 1, wherein said mean intensity data corresponds to uptake of FDG in said patient's brain.

5. The method of claim 1, wherein six regions of the brain are preselected for comparison, the six regions including the middle and superior temporal gyrus, the visual cortex, the motor cortex, the superior parietal area, and the frontal lobes.

* * * * *